(12) United States Patent
Medoff (10) Patent No.: US 9,237,911 B2
(45) Date of Patent: Jan. 19, 2016

(54) LOCKING PIN PLATE ASSEMBLY ADAPTED FOR FRACTURE FIXATION

(75) Inventor: Robert J. Medoff, Kailua, HI (US)

(73) Assignee: TRIMED, INC, Santa Clara, CA (US)

( * ) Notice: Subject to any disclaimer, the term of this patent is extended or adjusted under 35 U.S.C. 154(b) by 298 days.

(21) Appl. No.: 13/603,587

(22) Filed: Sep. 5, 2012

(65) Prior Publication Data

US 2013/0238035 A1 Sep. 12, 2013
US 2014/0135849 A9 May 15, 2014

Related U.S. Application Data

(63) Continuation-in-part of application No. 13/572,762, filed on Aug. 13, 2012, now abandoned, which is a continuation-in-part of application No. 12/533,675, filed on Jul. 31, 2009, now abandoned.

(51) Int. Cl.
*A61B 17/064* (2006.01)
*A61B 17/80* (2006.01)
*A61B 17/84* (2006.01)
*A61B 17/00* (2006.01)

(52) U.S. Cl.
CPC ........... *A61B 17/809* (2013.01); *A61B 17/8052* (2013.01); *A61B 17/846* (2013.01); *A61B 17/0642* (2013.01); *A61B 2017/00004* (2013.01)

(58) Field of Classification Search
CPC ........... A61B 17/7014; A61B 17/7059; A61B 17/80; A61B 17/8052; A61B 17/8061; A61B 17/064; A61B 17/0642; A61B 2017/00668

USPC ................... 606/280, 281, 286, 297, 75, 219
See application file for complete search history.

(56) References Cited

U.S. PATENT DOCUMENTS

| 5,810,822 A | 9/1998 | Mortier |
| 5,931,839 A * | 8/1999 | Medoff .......................... 606/286 |
| 6,692,507 B2 * | 2/2004 | Pugsley et al. ................ 606/153 |

FOREIGN PATENT DOCUMENTS

| EP | 0 723 764 A1 | 7/1996 |
| WO | 2004/091367 A2 | 10/2004 |

OTHER PUBLICATIONS

Supplementary European Search Report dated Dec. 12, 2013 for corresponding EP Application No. 10 80 4918.

\* cited by examiner

*Primary Examiner* — Anu Ramana
(74) *Attorney, Agent, or Firm* — Ladas & Parry LLP (57) ABSTRACT

A lockable pin plate assembly which has a pin plate adapted to be secured to stable bone and provided with pin holes for pins for pinning an unstable bone fragment. One or more pin holes are engageable by pins of an integral U-pin. The pins have stop surfaces thereon which are resiliently displaced when the pins are seated to automatically and self-lock the pin and the pin plate to oppose withdrawal and backing out of the pins from the pin plate. In a preferred embodiment, each pin of the U pin has a leading portion and a trailing portion, the leading portion being of smaller diameter to pass freely through an elliptical hole in the pin plate whereas the trailing portion is of larger size to become locked in the pin hole as it is advanced therein.

24 Claims, 12 Drawing Sheets

LOCKING PIN PLATE ASSEMBLY ADAPTED FOR FRACTURE FIXATION

CROSS REFERENCE TO RELATED APPLICATIONS

This application is a continuation-in-part of U.S. application Ser. No. 12/533,675 filed Jul. 31, 2009, now abandoned the content of which is incorporated herein by reference, and is a continuation-in-part of U.S. application Ser. No. 13/572,762, filed Aug. 13, 2012 now abandoned.

FIELD OF THE INVENTION

The invention relates to a lockable pin plate assembly for fracture fixation which includes a pin plate adapted to be secured to stable bone and a pin member for engaging an unstable bone fragment of the fracture and securing the fragment to the plate.

In particular, the invention relates to the pin member which serves to pin the unstable bone fragment and concurrently secures the pin member in locked engagement with the pin plate.

The invention further relates to a method for pinning the unstable bone fragment by a pin member while the pin member becomes lockably secured to the pin plate. In the case of fractures of the end of a bone, a small fragment can be produced which can be secured by the invention.

BACKGROUND

One common method of fixing fractured bones is to use a plate and screws to secure the bone fragments. In this method, screws are inserted through holes in the plate in order to secure the fragments to the plate. Although this technique is effective when the fragments are relatively large in relation to the diameter of the screw, when the fragment size is small in relation to the diameter of the screw, the size of the screw hole required in the bone fragment can weaken the fragment and cause it to fragment further, resulting in failure of fixation. Additionally, standard bone screws require thread purchase in the bone in order to compress the fragment against the undersurface of the plate in order to provide stability. If the fragments are small or consist of poor quality bone, thread purchase can be inadequate, resulting in failure of fixation.

In my previous U.S. patents (U.S. Pat. Nos. 5,931,839 and 7,044,951 plates have been disclosed that utilize small pins that are placed through the plate and into the bone fragments. This alternative type of fixation reduces the risk of causing additional fragmentation of a small fragment by reducing the hole size needed for fixation. In addition, since the pin does not depend on thread purchase in the bone fragment, this technique avoids the failure caused by poor purchase of screw threads.

Although the pin plates provide these advantages, the fixation by the pin is biomechanically different from that provided by a screw in a plate. In U.S. Pat. No. 5,931,839, the pin is not secured to the plate, but only restricts translational movement of the pin in relation to the surface of the plate. In this type of implant, axial movement of the pin in the hole as well as angulation of the pin within the hole are not constrained. If the pin is not rigidly secured into an opposite stable bone fragment, this may result in failure of fixation.

In U.S. Pat. No. 7,044,951 the pin is stabilized to the plate by modifications in the plate. Some of the modifications of the plate (FIGS. 3, 3A, 5, 6, 6A, 7, 8, 9, 10, 11, 12, 13, 14, 24, 25, 26) are constructed to provide a channel or aperture that prevents the pin from backing out of the bone. These embodiments limit axial movement of the pin but do not constrain angular movement of the pin. In other modifications (FIGS. 15, 16A, 16, 17, 18, 19, 20, 32, 33, 34, 35) the pin is captured by tabs on either side. These types of designs also limit axial movement of the pin out of the pin hole but do not limit angular movement of the pin in relation to the plate. In addition, they are cumbersome to manufacture and complicate the surgery by requiring the surgeon to bend and/or thread the end of the pin through the tabs in the plate. In still other modifications (21, 22, 23, 27, 28, 29, 31, 32, 33, 34, 25) the pin is constrained by frictional purchase of the plate against the side wall of the pin. Like the other embodiments, these modifications limit axial movement of the pin in relation to the plate, but provide less constraint to angular movement. In addition, most of these require the surgeon to crimp a portion of the plate with a bending instrument, which adds to the complexity of the procedure and may be difficult to do because of difficult access to the plate from a limited exposure. In addition, many of these embodiments require the pin to be bent or cut after the pin is in place which adds further to the complexity of the surgery. Finally, since many of these designs leave the end of the pin extending out of the plate, the cut end can cause irritation of the soft tissues and even tendon rupture.

SUMMARY OF THE INVENTION

An object of the invention is to provide a pin plate assembly in which pins can be utilized for fixation of the bone fragment and a locking mechanism is provided between the pins and the plate to cause the pins to become locked in the pin plate when installed in the fragment.

In accordance with the invention, a locking pin plate assembly is provided which includes a pin plate adapted to be secured to stable bone and having one or more pin holes in which a pin member can be inserted to an operative position for fixation of a bone fragment and wherein a locking mechanism is provided between the pin member and the pin plate to automatically self-lock the pin member in the plate when the pin member is inserted to its operative position.

In accordance with the invention, the locking mechanism has an unlocked state in which the pin passes through the pin hole and a locked state when the pin reaches the operative position.

The pin member can be in the shape of a U with adjacent legs which form pins connected by a cross member. The legs of the U pin are inserted through the pin holes and pin the unstable fragment and serve as an integral unit which, when seated on the pin plate, lockably secure the U pin to the pin plate to oppose withdrawal of the U pin from the plate.

The invention is further concerned with a particular construction of the pin plate.

The invention is also concerned with the method of automatic self-locking of the pin in the plate upon fixation of the unstable bone fragment.

It is a feature of the invention to provide locking of the pin in the pin plate without any additional instrumentation or complicated surgical techniques.

It is a further feature of the invention to provide a locking pin plate that restricts translational, axial, and angular movement of the pin in relation to the plate.

It is a further object of the invention to provide a pin that can be simply inserted and requires no cutting of the pin and leaves no end of the pin protruding in the soft tissue.

In further accordance with the invention, the pin and the hole are formed so that when the pin is in its operative position engaging the bone fragment, a clearance is formed between the pin in the hole and a force is produced on the pin to displace the pin in the hole to a lock position in which the pin is not removable from the hole.

In further accordance with the invention, the cross member of the U pin provides flexibility to develop the force to displace the legs of the pin.

In further accordance with the invention, the legs of the U-pin are provided, on external surfaces thereof, with grooves or ridges defining shoulders at the ends of the grooves which, when the U pin reaches its operative position seated on the pin plate, the legs flex and lock the shoulders at the end of the grooves or ridges against a surface of the pin plate to lock the U pin in the pin plate and oppose its removal.

In further accordance with the invention, the U pin may also be formed to have different diameters over its length. For instance, a larger diameter portion may be preferred for an intraosseous portion of the pin in order to provide greater strength to cantilever bending, while a smaller diameter portion may be preferred for an extraosseous portion of the pin in order to avoid soft tissue irritation.

In accordance with a preferred embodiment of the invention, the legs or pins of the U pin are formed with a first leading portion and a second trailing portion arranged to enter the respective pin hole in succession as the pin is longitudinally advanced in the pin hole. The first portion is shaped and dimensioned with respect to the pin hole to travel freely in the pin hole as the pin is longitudinally advanced in the pin hole. The second portion is shaped and dimensioned with respect to the pin hole to engage with an interference fit in the pin hole to produce the locking mechanism to lock the pin in the pin hole when the second portion has been advanced into the pin hole. More specifically, the pin hole has an elongated cross section with a major and a minor axis and the first portion has a maximum dimension aligned with the minor axis of the hole which is less than the dimension of the minor axis of the pin hole to enable its free passage therethrough. The second portion of the pin has a minimum cross section aligned with the minor axis of the hole which is equal to or greater than the dimension along the minor axis of the hole in order to produce the locking interference fit.

A typical sequence of insertion is to first apply and secure the plate to the stable bone fragment. A removable pin or drill is then drilled through the pin holes in the plate and into the unstable bone fragment to form pilot holes in the fragment. An appropriate size and contoured pin is then selected and impacted through the pin and pilot holes and into the unstable fragment. Impaction of the pin results in automatic, self-locking of the pin to the plate.

One typical application of this construction is for fractures of the medial malleolus of the ankle and is described herein. However, this is purely exemplary and other bone fractures are equally applicable, such as, the distal radius or distal humerus, spine and other bones. In addition, although the examples used herein describe a plate with the locking pins at one end, this type of locking pin plate design is equally applicable for placement in any position over the length of the plate. For example, locking pins could be used in the central portion of a plate for fixation of shaft fractures or over the entire length of the plate for stabilization of spinal elements.

DETAILED DESCRIPTION OF THE INVENTION

Figure 1:
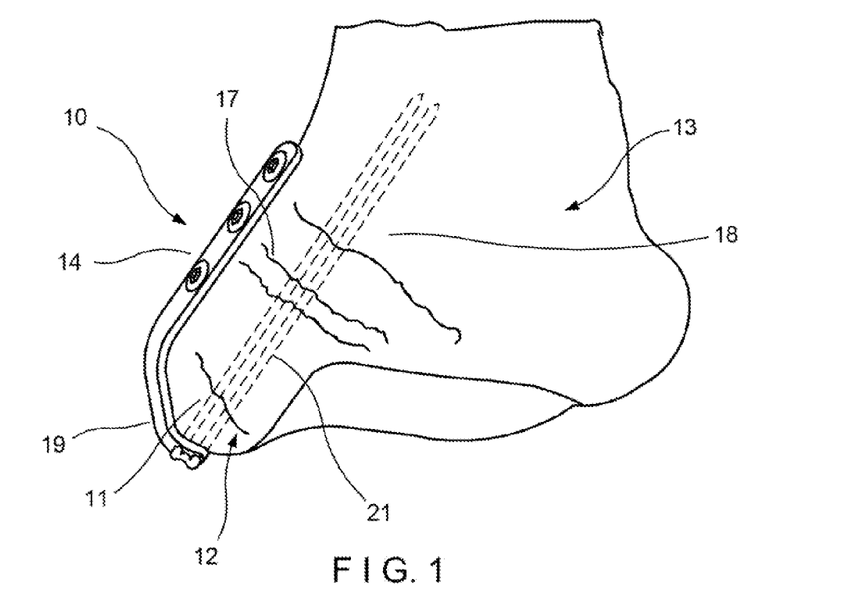
FIG. 1 is a diagrammatic, side elevation view, partly broken away, showing the installation of the pin plate assembly on a fractured bone of the ankle.
Figure 2:
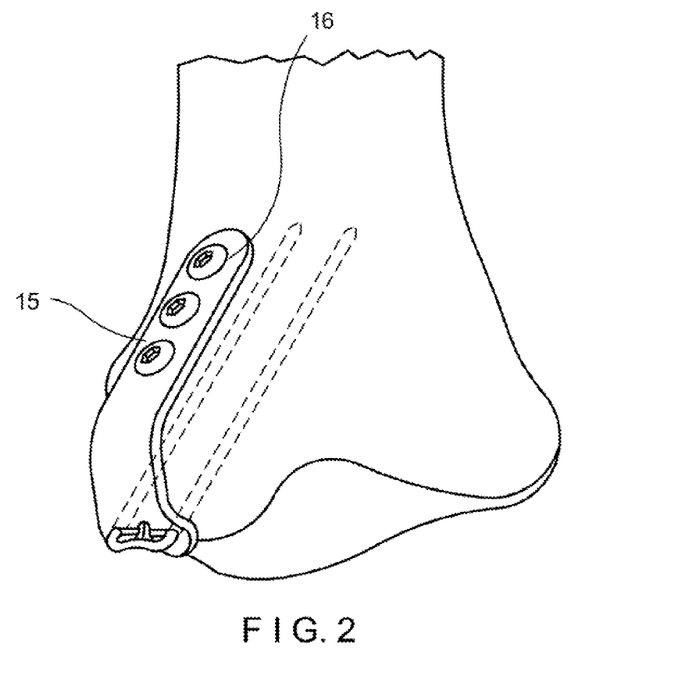
FIG. 2 is a perspective view of the installation shown in FIG. 1.

Referring to FIGS. 1 and 2 therein is shown a pin plate assembly 10 adapted for fixation of a small fragment 11 of a bone fracture 12 of the medial malleolus of the distal tibia bone 13 which is adjacent to the ankle.

Although the pin plate assembly 10 is described for fixation of the fracture 12 of the ankle bone 13, this is for exemplary purposes only and the pin plate assembly is applicable to fractures of all bones.

By way of example of other fracture sites are the lateral/medial condyle or epicondyle of the elbow, proximal shoulder, distal fibula, olecranon, proximal/distal radius, distal ulna, and even metacarpal/metatarsal bones or phalangeal bones of the hand or foot or stabilization of spinal elements.

The pin plate assembly comprises a pin plate 14 having a first portion 15 with holes 16 adapted for receiving at least one fastener 17 in the form of bone screws for securing the first portion to stable bone 18. Although the expression "bone screws" is used for simplicity in the description of securing the plate to bone, the fastener 17 is not limited to screws. In other embodiments pins, wires, blades, staples, brackets, or indirect coaction with another device securely attached to the stable bone fragment through holes in the plate are used.

The pin plate 14 is shaped to fit on the bone and includes a second portion having pin holes 20 at the distal end adapted for receiving at least one pin 21 for engaging the unstable bone fragment 11. In the illustrated embodiment, the pin 21 pins the unstable fragment to stable bone 18. However, as will be seen later, the pin may only be pinned to the unstable fragment.

Figures 3, 4:
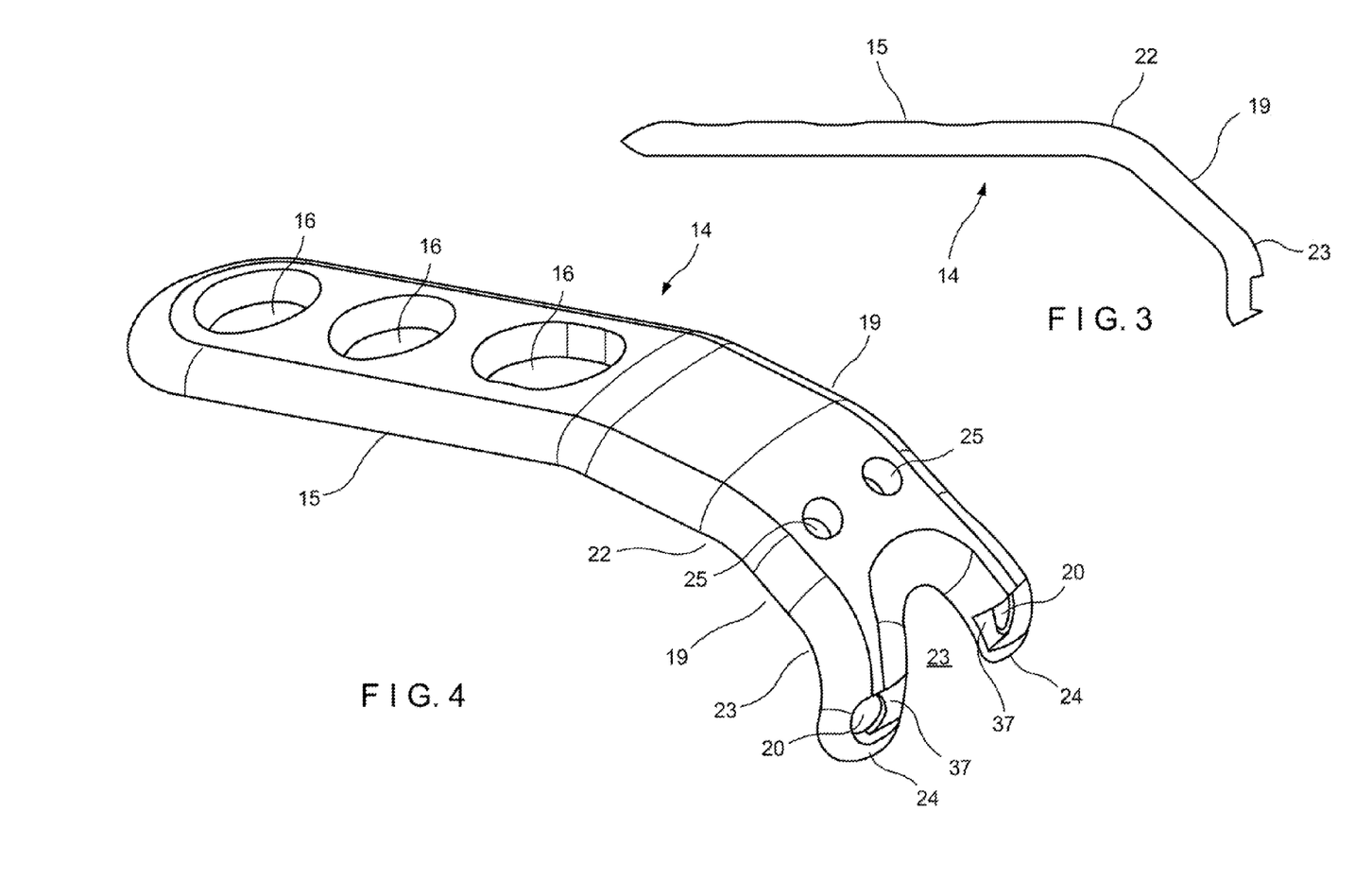
FIG. 3 is a side elevational view of the pin plate of the pin plate assembly.
FIG. 4 is a top perspective view from the right, of the pin plate in FIG. 3.
Figure 9:
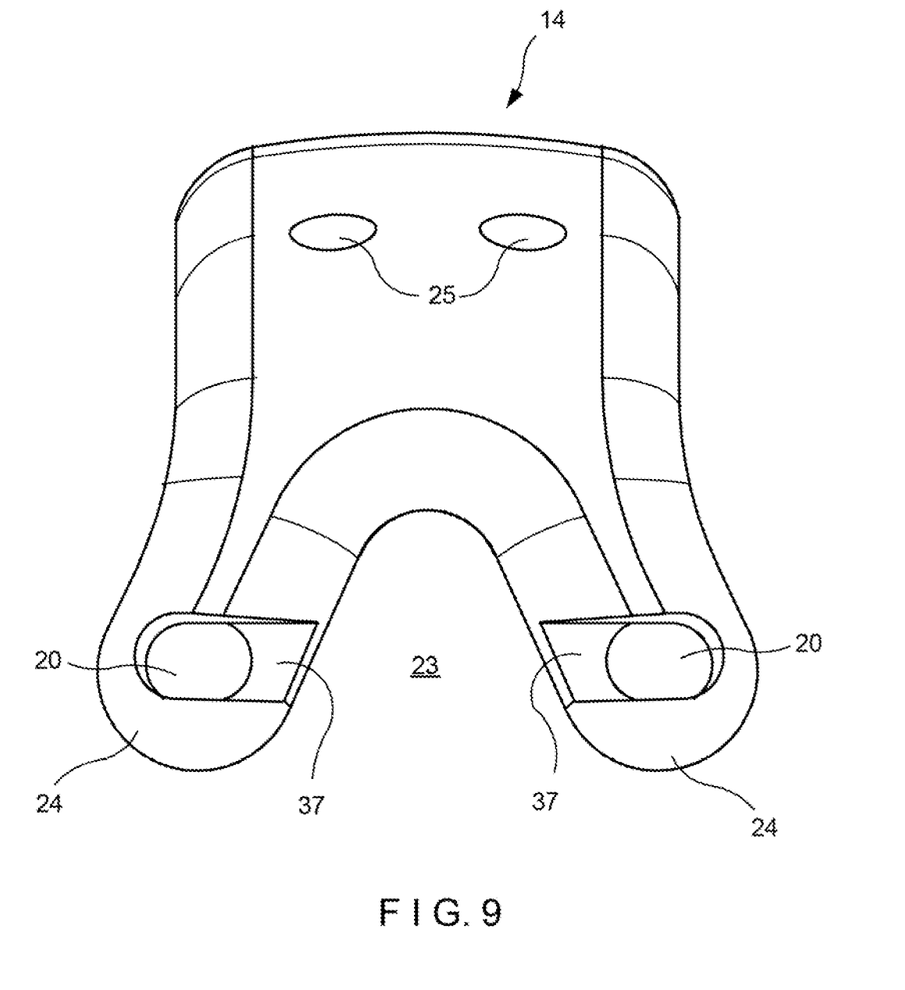
FIG. 9 is an end view of the pin plate from the right side of FIG. 4.

As best shown in FIGS. 3, 4 and 9, in one embodiment the pin plate has a first bend region 22 of about 45° and a second bend region 23 so that the distal end of the pin plate is predominantly perpendicular to the longitudinal axis of the pin plate.

As best seen in FIGS. 4 and 9, the distal end of the pin plate 14 has a U shaped opening 23 which forms legs 24 on opposite sides of the opening 23. The legs 24 are slightly flared away from one another to provide an increased spacing of the pin holes 20. A pair of guide holes 25 is provided in the plate more proximal than the pin holes 20 and can serve for installation of conventional pins or bone screws for temporary fixation of the bone, or as an attachment site for a drill guide.

Figure 5:
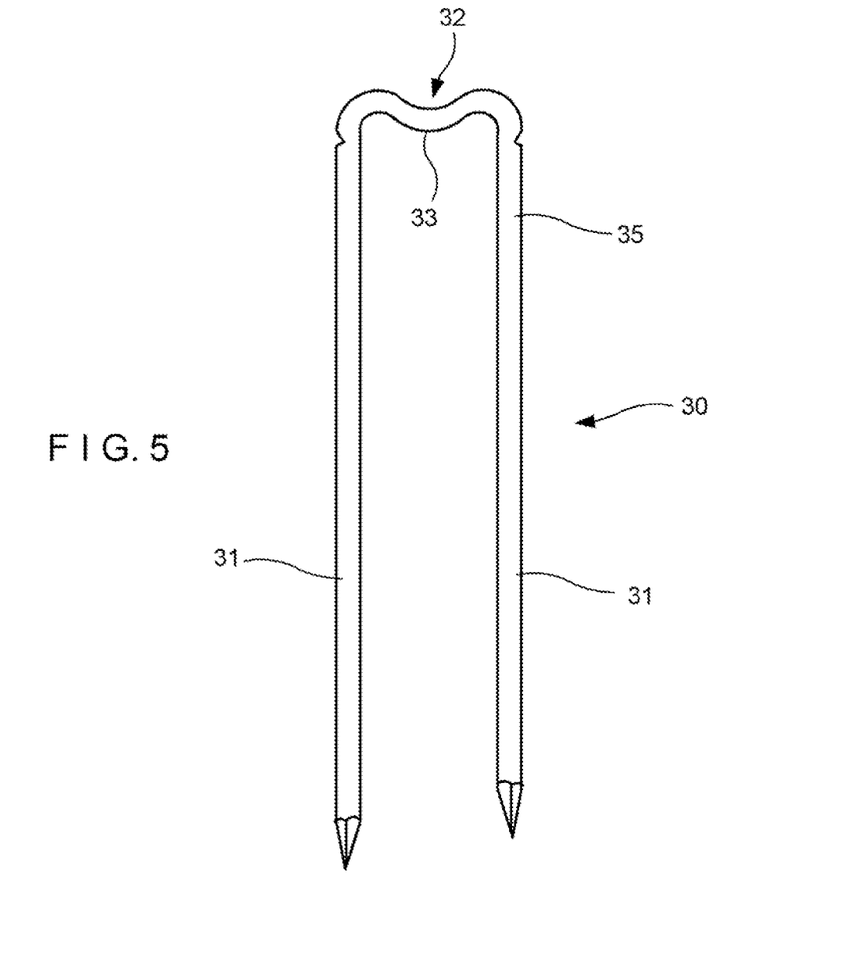
FIG. 5 is a front elevation view of a U pin of the pin plate assembly.
Figure 6:
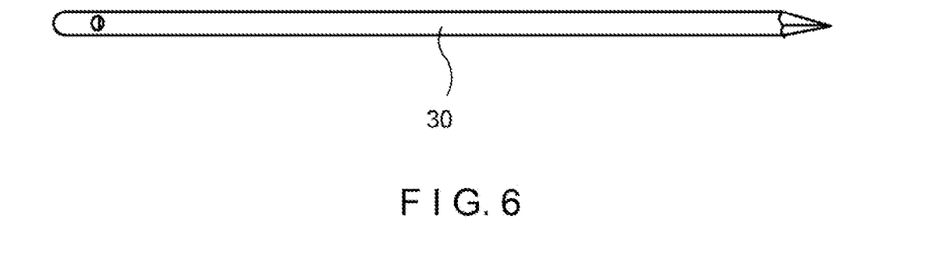
FIG. 6 is a side elevation view of the U pin.

In order to pin the unstable bone fragment, a pin member in the form of a U as shown in FIG. 5 and hereinafter referred to as a U-pin 30 is utilized. The U pin 30 has a pair of generally parallel legs 31 forming pins which are connected by a cross piece 32 to provide the base for U pin 30. In the illustrated embodiment the cross-piece 32 is formed by a bend which provides additional flexibility of the legs at the ends of the bend where they are joined to the legs.

The U pin 30 is formed as a bent wire and has a diameter based on the bone being pinned. Alternatively, but not shown, the U pin may have differing diameters between a portion of the leg members 31 and a portion of the cross-piece 32. The diameter of pinning members is well known to those skilled in the art. The pin plate 14 has a size related to the bone being repaired and in general can vary from a thickness of 0.020 to 0.250 inches. In general, the pin plate is relatively stiff and resists bending. However, under certain circumstances, the pin plate can be made flexible so that the pin plate is pushed against the bone as it is screwed into the bone.

The pin and the pin plate are made of conventional material such as stainless steel, titanium or titanium alloys, PEEK, or other suitable polymers and bioabsorbable material.

The ends or tips of the pins 31 are pointed to facilitate penetration of the tips into bone. In another embodiment, the tips are bullet shaped.

The cross piece 32 has an inward dimple 33 which serves a purpose to be explained later. The dimple 33 also provides flexibility at the base of the U pin also for a purpose to be explained later.

Figure 7:
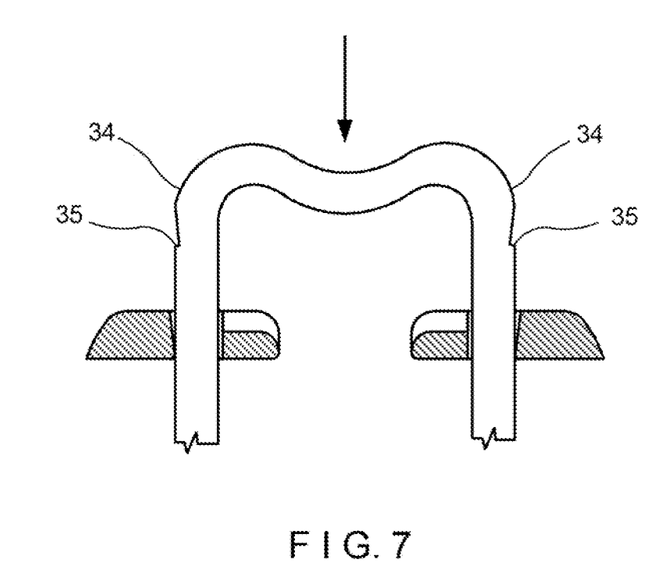
FIG. 7 shows, in end view, the installation of the U pin in the pin plate before the U pin is fully seated on the pin plate.
Figure 8:
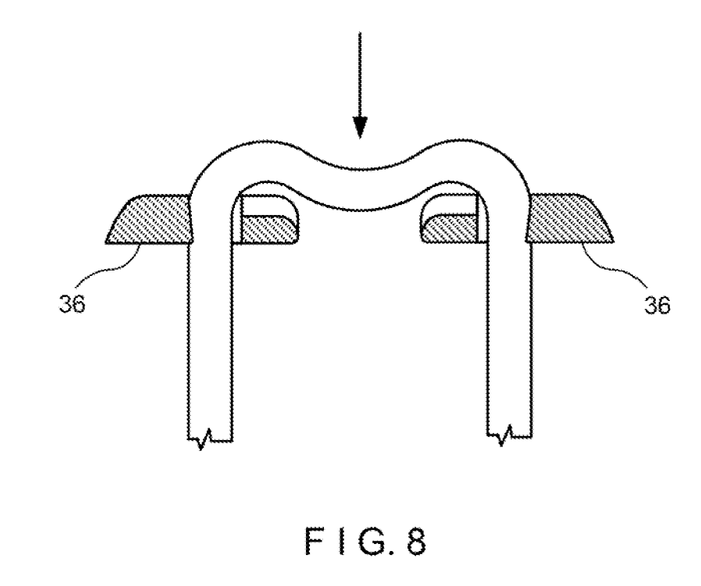
FIG. 8 is similar to FIG. 7 after the U pin is fully seated on the pin plate.

The U pin 30 is provided with grooves or notches 34 on the outer surfaces of the legs 31 extending downwardly from the cross piece 32. The grooves form stop surfaces serving as shoulders 35 or shelves at the ends of the grooves 34. The grooves 34 and shoulders 35 are best seen in FIGS. 7 and 8. The grooves 34 and shoulders 35 form part of the locking mechanism for automatically self-locking the pin in the pin holes in the plate. Although shown in this drawing on the outer surface of the pin, they could be formed on any external surface of the pin. Instead of forming grooves or notches on the outer surfaces of the pins, the pin surfaces can be crimped to form indentations along one cross-sectional axis and produce shoulders 35 along the perpendicular cross-sectional axis. The width of the cross piece or bend of the U pin is equal to or slightly greater than the spacing between the pin holes 20 in the legs 24 when the grooves are on the outer surfaces of the legs 31 and when the grooves are on the inside surface of the legs, the spacing is equal to or slightly less than pin spacing.

In order to achieve fixation of the fracture, first the fracture is reduced and then the bone screws 17 are utilized to secure the pin plate to stable bone. Two pilot holes are then drilled in the unstable fragment through the pin holes 20. In the case of the medial malleolus, the pilot holes only need to penetrate the cortex of the unstable fragment whereafter the U pin is then impacted into the bone fragment by simple hammering it in.

Referring to FIGS. 7 and 8, it is seen in FIG. 7 that before the U pin is fully seated in the pin plate, the legs 31 of the U pin tightly fit in the pin holes and resiliently bear against the outer walls of the pin holes due to the resilience afforded by the cross piece as well as angular bends in the pin and the spacing of the legs with respect to the spacing of the pin holes. In a preferred embodiment, the spacing between the legs 31 in a rest state is slightly greater than the spacing between the holes 20 in the plate so that the legs 31 of the U pin are squeezed together under tension in order to engage the holes 20. When the grooves 34 on the outer surfaces of the legs 31 enter the pin holes and pass therein and the U pin is fully seated in the pin holes, as shown in FIG. 8, the pins automatically snap outwardly to position the shoulders 35 beneath the edge of the undersurface 36 of the pin plate. This securely locks the U pin in place on either side in the pin holes 20 in the legs 24 of the pin plate. In this way, the U pin cannot back out of the pin plate and a secure locking engagement of the U pin in the pin plate is achieved.

In a preferred embodiment, the diameter and direction of holes 20 in plate 14 are directed for optimal fixation at the site of application. The orientation of the hole may be designed to optimally locate the legs 31 of U pin 30 in the unstable bone fragment. In addition, the difference between the inner diameter of holes 20 in plate 14 and the outer diameter of legs 31 of U pin 30 is preferably large enough to allow passage of the legs 31 through the holes 20, yet with tolerances that are tight enough when the pin is fully seated to limit angular movement of the legs 31 in holes 20.

Although the grooves 34 have been shown on the outer surfaces of the pins it is equally possible to place the grooves on the inner or outer surfaces of the pins. If placed on the inner surfaces of the legs 31 of U pin 30, the width of the bend at the cross piece of the U pin would be made equal to or slightly smaller than the spacing between the pin holes 20 so the pins will snap inwardly to lock the shoulders 35 under the plate. In an alternative embodiment, the groove may be present on only one leg of U pin 30.

Although pin plate assembly 10 is illustrated with the locking U pin at one end of the pin plate and the bone screws at the other end, it is possible to have locking U pins in a central portion of the plate, at either or both ends of the plate, or throughout the length of the plate. In addition, although pin plate assembly 10 is demonstrated with bone screws at one end, it is possible to have a pin plate assembly in which no bone screws are used but rather the plate is secured only with locking pins at either end or centrally in the plate.

The dimple 33 which faces inwardly between the legs provides slight resilience for the cross piece to enhance the resilient force on the pins and promote the snap engagement of the shoulders 35 with the undersurface 36 of the pin. Alternatively, the cross piece between the legs 31 of the U-pin 30 can be bent outwardly from the plane formed by the legs 31 of U-pin 30. By varying the length of the cross piece out of the plane of legs 31 and the diameter of the cross piece the amount of resilience can be varied to provide a lateral force of the pin on the side wall of the pin hole that is appropriate for the site of application.

The pin plate 14 is provided with grooves or cutouts 37 as shown in FIGS. 4 and 9 that extend from the pin holes 20 to the U shaped opening 23. The cutouts 37 are shaped and dimensioned to allow the cross piece 32 of the U pin to seat almost flush against the end of the pin plate when fully seated thereby avoiding any protruding corners or sharp ends that might irritate soft tissue. In addition, the dimple 33 allows the cross piece to sit flush against the bone surface between the legs 24 and avoid irritation of soft tissues.

In prior pin plate assemblies, there was little angular stability of the pin in the pin hole of the plate. In contrast, the pin plate configuration of the current invention is substantially stable and as previously recited; the U pin will not back out of the pin plate. Additionally, since the engagement of the pins in the pin holes is achieved with a single U pin engaged in two distinct pin holes separated by a fixed distance, the U pin is rigidly held by the pin plate and won't angle from side to side. In addition, the relatively tight fit of the pin within the hole of the pin plate coupled with the pressure of the pin against the side wall from the resilience of the cross piece 32 as well as the lock of the shoulder against the edge of the plate serves to restrict angular movement of the pin in the pin hole. With the present invention the U pin which is a single structure that is held relatively rigidly in the holes by the lock between the shoulder 35 against the undersurface 36 of pin plate 14. Because of this intrinsic stability, there is no need to capture a far cortex with the pin but rather one or both legs of the U pin can terminate within the metaphyseal bone. Thus, pinning of the bone fragment only requires the pin to extend into the fragment and not through the fragment and into and through stable bone. This greatly simplifies the surgical technique since the surgeon does not have to measure the pin length, withdraw the pin, cut the end of the pin to length and form a hook on the end of the pin and then re-impact the pin into the bone. Instead, according to the invention, the surgeon simply drills the pilot holes and hammers the U pin in place thereby providing automatic locking of the shoulders against the undersurface of the pin plate at the edges of the pin holes and integral locking of the pin with the plate.

In essence, it is the flexibility of the cross piece 32 and the angular bends of the U-pin 30 and the grooves 34 with shoulders 35 that snap into their respective pin holes 20 and lock the U-pin to the pin plate. Hence, the locking mechanism between the pin and the pin plate is initially in unlocked state and the pin passes through the pin hole to the operative position whereupon the pin is shifted and the locking mechanism automatically self locks the pin in the pin plate in locked state. This allows the pin to be slightly oversized or undersized so that as the pin is seated, the tendency to return to the initial position of the U pin, engages the shoulder 35 against the undersurface of the plate.

Although the U-pin has been shown as having two legs or pins 31, it is also possible to utilize only a single pin with at least one leg formed with shoulder 35 to lock the pin in the pin plate. In such case, the locking pin would have an L-shape, J-shape, or shape similar to a nail. Accordingly, even though the pin member has been referred to as a U-pin, it is to be understood that this term also refers to other shapes as described above.

In addition, although the current description shows a plate 14 with two holes 20 for engagement of the two legs 31' of U-pin 30, it is also possible to have a plate with a single hole for one leg 31 of U-pin 30, with the other leg abutting against the side of the plate.

The current description demonstrates a locking mechanism in which the shoulder 35 of groove 34 of U-pin 30 that locks against the bottom edge of the pin hole 20 in the plate. It is also evident that this locking mechanism could be designed with an edge or ridge within the pin hole as well, without affecting the spirit of the invention. For instance, a ridge within the hole could engage the groove on the U-pin.

Figure 10:
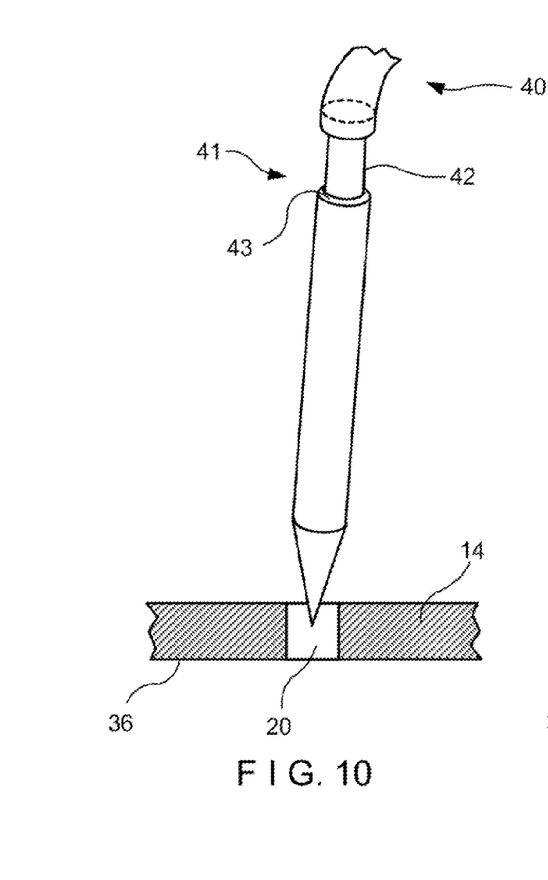
FIGS. 10-16 diagrammatically illustrate variations of the pin and pin plate assembly.

In the disclosed embodiments, the lateral displacement of the pin in the hole is provided by the flexibility of the pin itself and its elastic deformation when the pin is relaxed to shift the stop surface into engagement with the pin plate to lock the pin in the pin hole. In another arrangement, the pin hole can be made elastic as for example shown in my published application (U.S. Ser. No. 11/103,923) so that when a slightly oversized pin is inserted into the hole, the wall of the hole will yield and when the portion with the groove reaches the bottom of the hole, the wall itself will relax and urge the pin laterally against the wall and lock the stop surface under the plate. FIG. 10 illustrates a variation of the pin shown in FIGS. 7 and 8. Instead of forming a groove at one side surface of the pin, as in FIGS. 7 and 8, the leg 41 of pin 40 is formed with a reduced cylindrical portion 42 forming an annular shoulder 43. The installation and engagement of pin 40 in the pin hole 20 in pin plate 14 to automatically self-lock the pin 40 in the plate 36 serves to prevent its withdrawal and backing out of the hole similar to FIG. 8.

Figure 11:
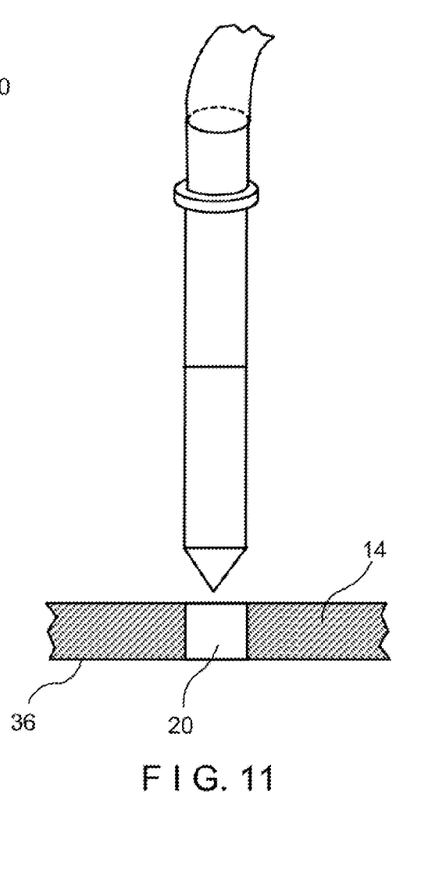

FIG. 11 shows another variation. Therein, the leg 51 of pin 50 is formed with a ridge 52 partially or completely around the pin. The outer diameter of ridge 52 corresponds to the inner diameter of pin hole 20 in plate 14 but is slidable therein. The diameter of the remainder of the shaft of leg 51 is less than the diameter of ridge 52. As before, the pin is driven through the pin hole into the bone fragment. Near the end of the travel of the pin, the ridge 52 enters the pin hole and passes therethrough whereupon, the pin is laterally displaced by the resilient force of the pin member to automatically engage the ridge 52 under the undersurface 36 of pin plate 14 to lock the pin and prevent its withdrawal from the hole.

Figure 12:
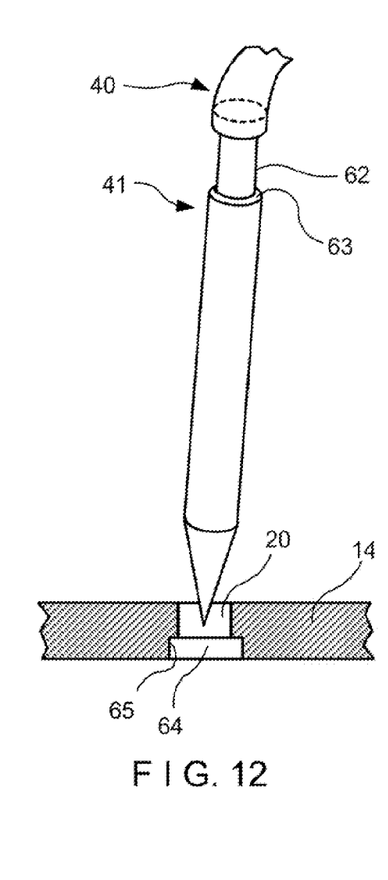

FIG. 12 shows another variation of the engagement of the U-pin 40 and pin plate 14. Therein, the pin 41 is formed similarly to FIG. 10 with a reduced diameter portion 62 forming an annular shoulder 63. The pin hole 20 in pin plate 14 is formed with a countersink 64 at its lower end to form a ledge 65 at the juncture between pin hole 20 and countersink 64. As in the previous arrangements, the pin is driven through the pin hole 20 into the bone fragment. When the shoulder 63 passes the ledge 65, the pin is elastically urged outwards (to the left in FIG. 12) and the shoulder snaps beneath the ledge to automatically lock the pin in the pin hole to prevent its withdrawal and backing out from the hole. Because the shoulder 63 engages the recessed ledge 65 in hole 20, the reduced diameter portion 62 is less in length than that in FIG. 10 by an amount substantially equal to the depth of countersink 64.

Figure 13:
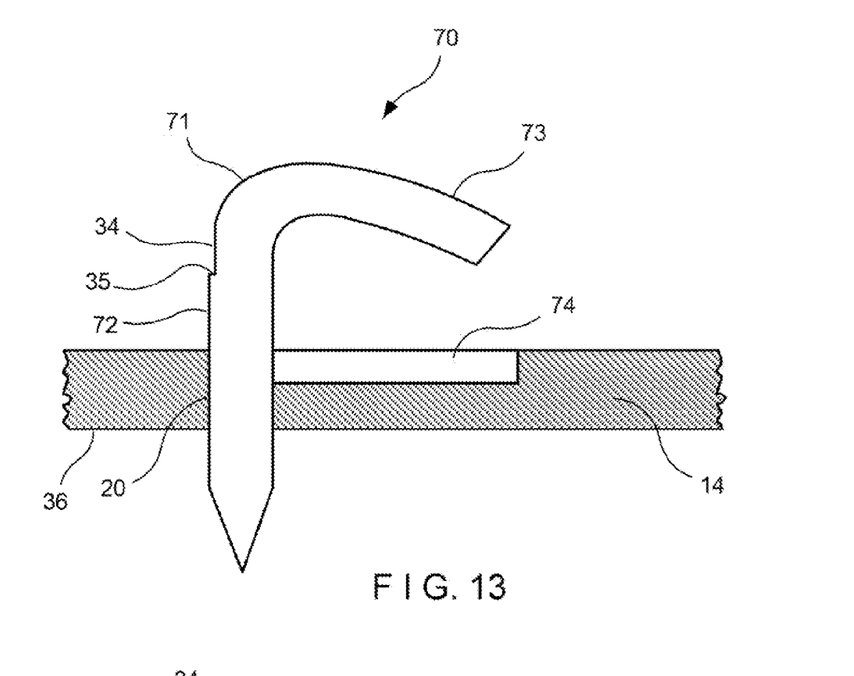

FIG. 13 shows another embodiment of a pin 70 for automatically locking in a pin plate 14. In this embodiment, the pin 70 is bent at bend 71 to form legs 72 and 73. The legs 72 and 73 form an acute angle therebetween. The plate 14 is formed with a recess 74 in its upper surface similar to the cut-out 37. The outer surface of leg 72 is formed with a groove 34 forming a shoulder 35 as in the earlier described embodiments. As before, the leg 72 of pin 70 is driven through pin hole 20 in pin plate 14 into the bone fragment to be pinned. When the groove 34 enters the pin hole, the leg 73 contacts the pin plate at the bottom of recess 74. As the pin is further advanced in the pin hole, the leg 73 flattens out to increase the angle between the legs 72 and 73 and apply a resilient force on leg 72 to press leg 72, against the outer wall of hole 20. When the shoulder 35 passes the lower surface 36 of plate 14, the shoulder 35 snaps under surface 36 to automatically lock the pin in the pin plate.

Figure 14A:
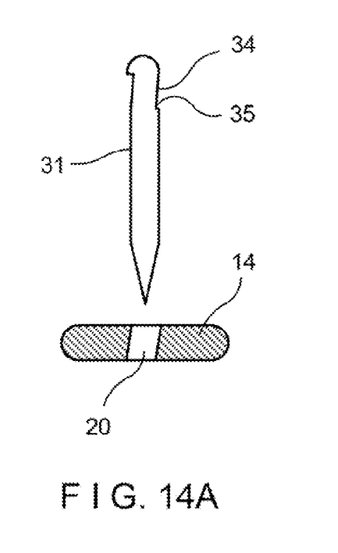
Figure 14B:
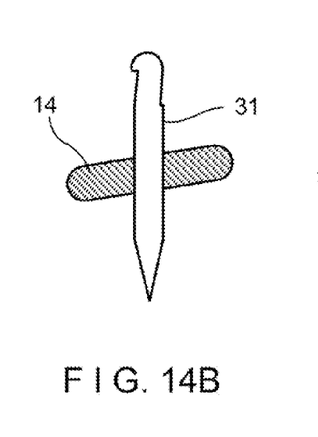
Figure 14C:
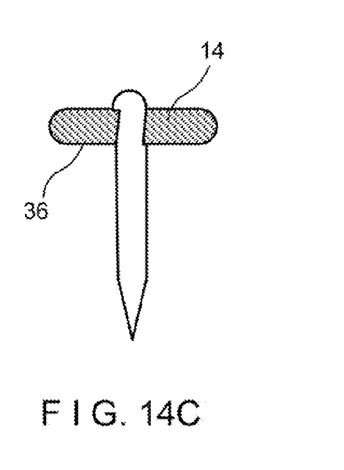

FIGS. 14A-C illustrates an embodiment in which the plate exerts resilient force to shift the pin laterally to its locked position. Referring to FIG. 14A, therein is seen pin 31 with groove 34 therein in readiness to be inserted into hole 20 in pin plate 14. In contrast with the previous embodiments, the hole 20 is inclined in the pin plate. FIG. 14B shows the pin 31 partially inserted into hole 20. Due to the inclination of the hole, when the pin is driven straight in, perpendicular to the plate, the plate is elastically deformed as shown in FIG. 14B. When the groove 31 on the pin passes through the hole and shoulder 35 exits from the bottom of the hole, the plate 14 returns to its initial state and urges the pin laterally to engage the shoulder 35 under the undersurface 36 of the plate to lock the pin against withdrawal and backing out from the hole In the previous embodiments, the pins are cylindrical, the holes are circular, and the stop surface is formed by a shoulder at the bottom of a groove in the external surface of the pin or by a ridge that is seated against the undersurface of the plate. However, the pins can have different cross-sectional configurations, the holes can be non-circular and the stop surfaces can be formed as part of the cross-section of the pin as shown hereafter.

Figure 15A:
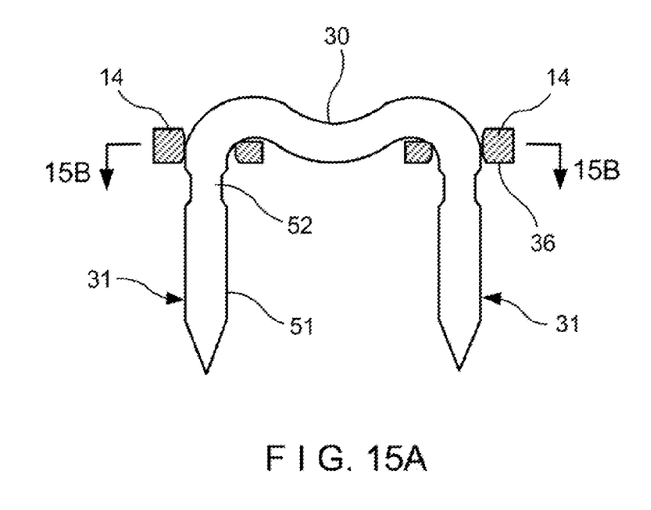
Figure 15B:
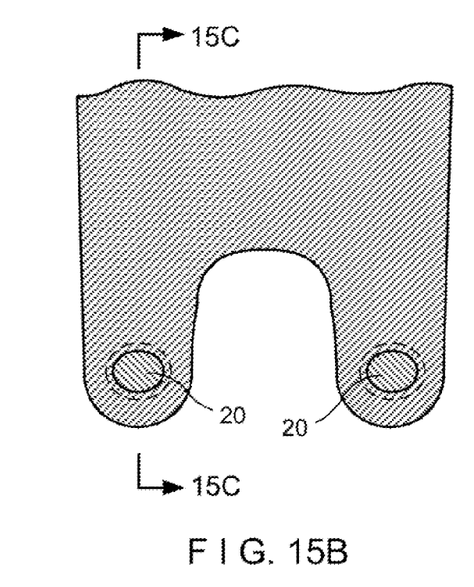
Figure 15C:
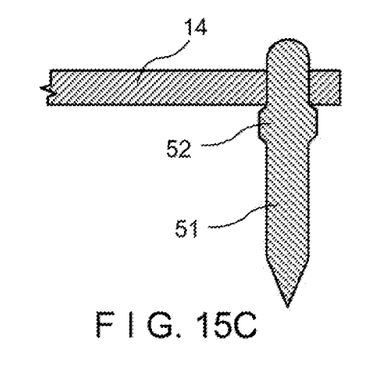

FIGS. 15A-C show an embodiment in which U-pin 30 is installed in pin plate 14 and where the legs 31 of U-pin 30 are crimped rather than formed with grooves. In particular, each leg 31 has a first portion 51 and a second portion 52, portion 52 being crimped to define an elongated cross-section of substantially elliptical shape, while the first portion 51 has a circular shape. When the legs 31 of the pin 30 are driven through the pin holes 20 and into the bone fragment, the circular portion 51 passes through the hole. The length of the major or long axis of the elliptical cross-section of portion 52 is equal to the diameter of the hole 20. When the top of elliptical portion 52 passes through the bottom of the hole, the elastic force of the U-pin forces the legs 31 outwardly to automatically cause the tips of the elliptical portion to shift laterally behind the undersurface of the pin plate 14 and form a stop surface to prevent withdrawal or backing out of the pin from the hole as shown in FIG. 15C. The shift of the pin in the hole can be of the order of a few thousandths of an inch to provide locking of the pin legs in the holes.

In a variation, the pin hole 20 can be elliptical in cross-section with the short axis of elliptical hole 20 corresponding to the long axis of elliptical portion 52. After the elongated axis of portion 52 passes beyond the short axis of elliptical hole 20, the leg 31 can laterally displace to the tip of the long axis of pin hole 20 thereby locking the elongated portion 52 under the surface of the plate. In another modification, the elliptical portion 52 can be oversized in a circular pin hole. The pin hole elastically expands slightly when the elliptical portion 52 passes through the hole, and when the elliptical portion exits from the bottom of the hole, the hole relaxes to its initial state and the circular portion 51 is automatically displaced laterally to bear against the side of the hole and the elliptical portion 52 is locked behind the bottom of the pin plate.

Preferably, in the above variations, the legs 31 of the U-pin are made divergent to produce tension in the pin and enhance the elastic action to displace the legs against the wall of the hole when the pin reaches its operative position.

In the embodiment of FIGS. 8 and 10-14 the operative position is reached when the grooved portion of the pin leg is in the pin hole, whereas in FIG. 15 and its variants, the operative position is reached when the crimped portion has passed through the hole in the pin plate.

Figure 16A:
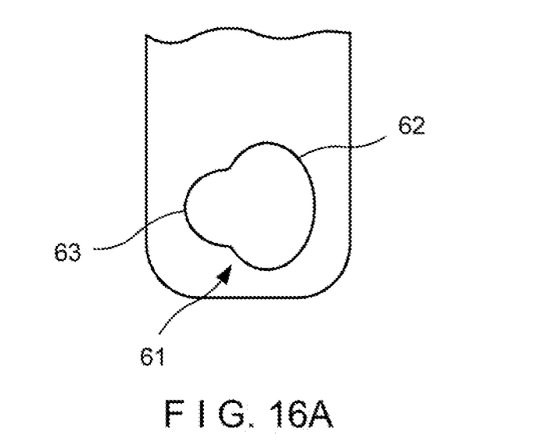
Figure 16B:
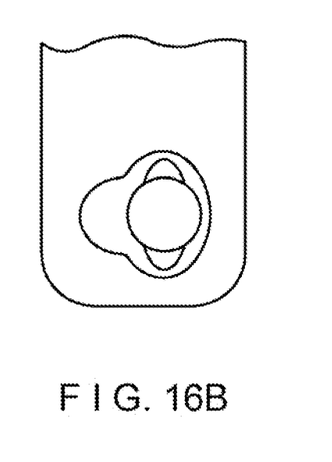
Figure 16C:
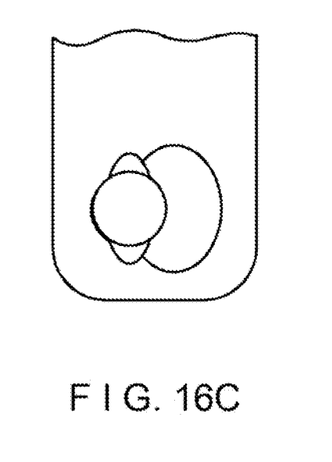

FIGS. 16A-C show another arrangement in which the pin hole 61 in the pin plate 14 has the shape illustrated in FIG. 16A. In particular, the pin hole 61 has a part elliptical cross-section 62 with a part-circular extension 63 at one side thereof. The pin has a circular cross-section in portion 51 and an elliptical crimped portion 52 as shown in FIG. 15A.

The pin is driven through the hole and the elliptical portion 52 aligns in the elliptical portion 62 of the hole as shown in FIG. 16B. When the crimped portion 52 passes the bottom of the hole, the pin is automatically displaced laterally so that the circular portion of the pin fits into the circular part 63 of the hole whereupon the tips of the crimped portion 52 are positioned behind the bottom surface of the pin plate to lock the pin to prevent its withdrawal and backing out of the pin plate.

Figure 17:
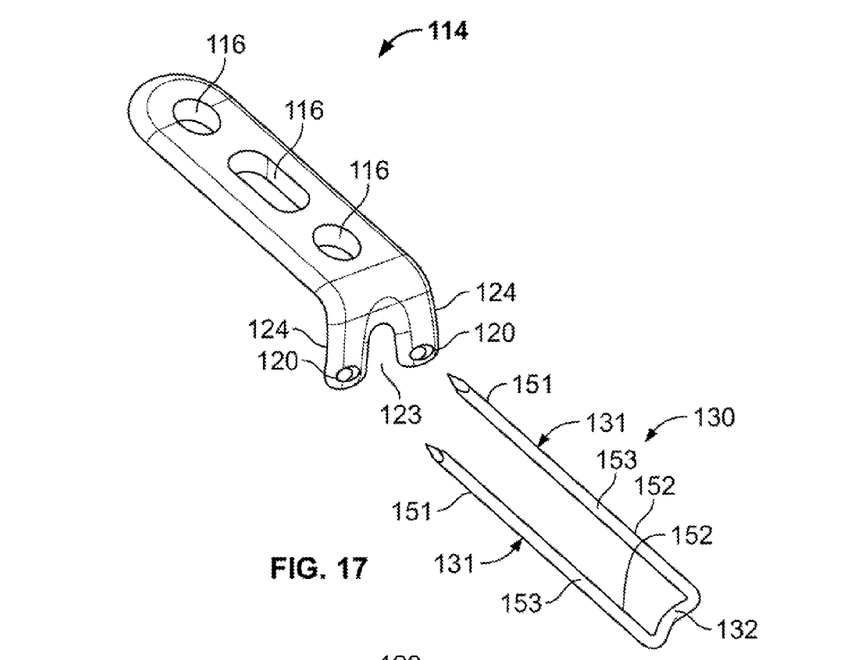
FIG. 17 is a perspective view of a pin plate and a U-shaped pin ready for insertion therein according to another embodiment according to the invention.

FIGS. 17-23 show a further embodiment according to the invention. In FIG. 17 there is shown a perspective view of a pin plate 114 and a U shaped pin member hereafter referred to as a U pin 130 adapted for locking engagement in elongated pin holes 120 provided in spaced legs 124 on opposite sides of a U shaped opening 123 similar to FIGS. 4 and 9. The pin plate 114 is provided with holes 116 for passage of bone screws (not shown) to secure the pin plate to stable bone. The U pin 130 comprises two pins 131 adapted to pass through pin holes 120 to engage a bone fragment, in an operative position of the pins, for fracture fixation. In said operative position of the pins in engagement with the bone fragment, the pins are locked in the pin holes as will be explained subsequently.

Each pin 131 is provided with a first or lower portion 151 for engaging the bone fragment and a second portion 152 at the upper end of the pin 131. A cross-piece 132 connects the upper portions of the pins to confer the U shape for the U pin 130.

The first portion 151 has a smaller diameter than the second portion 152 and a transition portion 153 joins the first and second portions 151 and 152. At its lower end the transition portion has a diameter substantially equal to the diameter of the first portion and at its upper end it has a diameter substantially equal to the diameter of the second portion.

Figure 18:
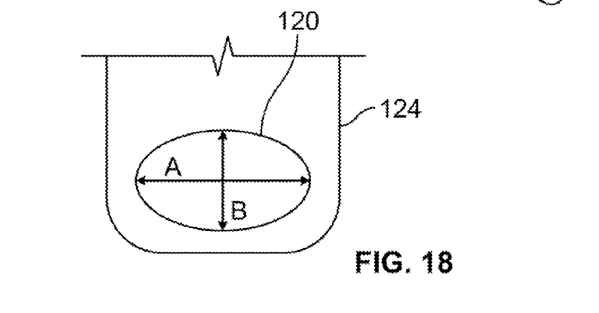
FIG. 18 is an enlarged front view of a pin hole in the pin plate.

FIG. 18 is an enlarged front view of a portion of leg 124 with hole 120. The hole in the other leg is the same. The hole is elongated and substantially elliptical having a longer major axis A and a shorter minor axis B.

The diameter of the smaller first portion 151 is less than the length of the minor axis B of the hole 120 so that the first portion of the pin will pass freely through the hole when the pin is advanced through the hole.

Figure 19A:
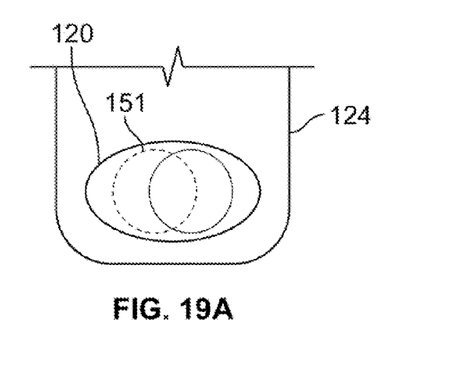
FIG. 19A is an enlarged front view diagrammatically illustrating a small diameter portion of a pin in the left pin hole of the pin plate in FIG. 17 for a wider spacing of the pins.
Figure 19B:
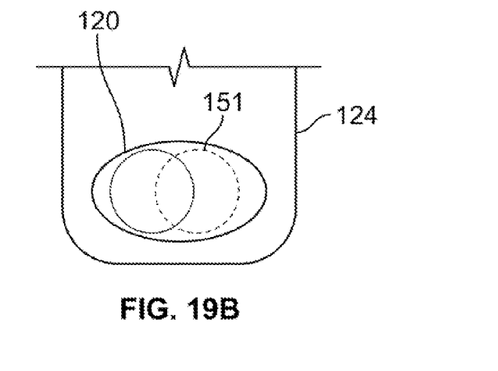
FIG. 19B is similar to FIG. 19A showing a narrower spacing of the pins.

Normally the pins will be centered in the holes in the pin plate, however, if the spacing of the holes 120 is less than the spacing of the pins 131 the position of the pins in the holes will be shifted outwardly as shown for the left leg of the pin plate in FIG. 19A. Conversely if the spacing of the pins is less than the spacing of the holes, the pins will be shifted inwardly as shown in FIG. 19B. Normally the pins will be centered in the holes in the pin plate. However the longer major axis of the hole A allows free passage of the smaller diameter portion 151 through the hole for variation of the separation of legs 131 of U pin 130. As shown in FIGS. 19A,B, the major diameter of the hole accommodates free passage of the legs 151 of a U-pin with a greater separation as well as another U-pin 151*b* (solid circles) with a smaller separation between the legs. This, however, will not affect the free passage of the smaller diameter portion 151 through the elliptical hole 120 nor its lateral displacement.

Figure 20A:
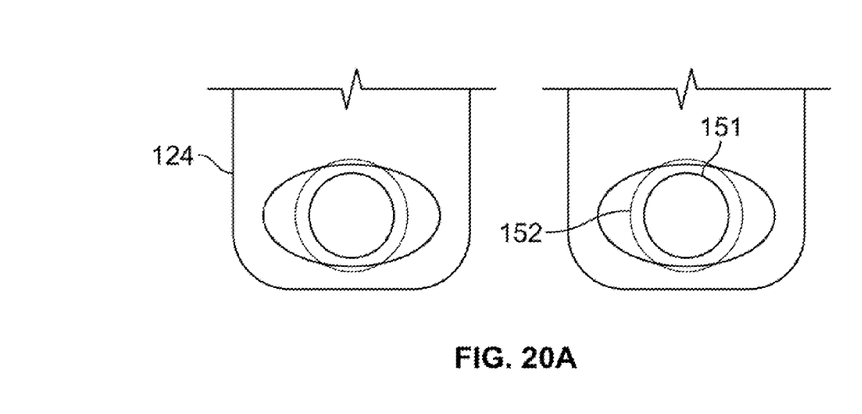
FIG. 20A shows the pins after advancement thereof in the pin holes in readiness for being locked in the pin holes.
Figure 20B:
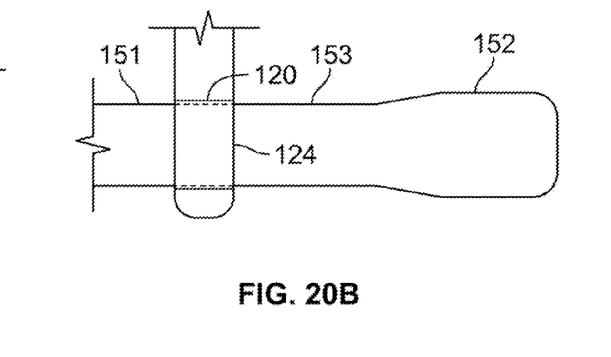
FIG. 20B is a side view of FIG. 20A showing the pin in the pin hole where the smaller portion of the pin has partially passed through the pin hole.

FIG. 20B is a side view showing the pin in the hole after advancement of the smaller diameter portion 151 through the pin hole 120 up to the beginning of the transition portion 153.

FIG. 20A shows the position of the first portion of the pin in the pin hole where the smaller diameter portion 151 has entered the hole, but the larger diameter portion 152 has not yet entered the hole.

Figure 21A:
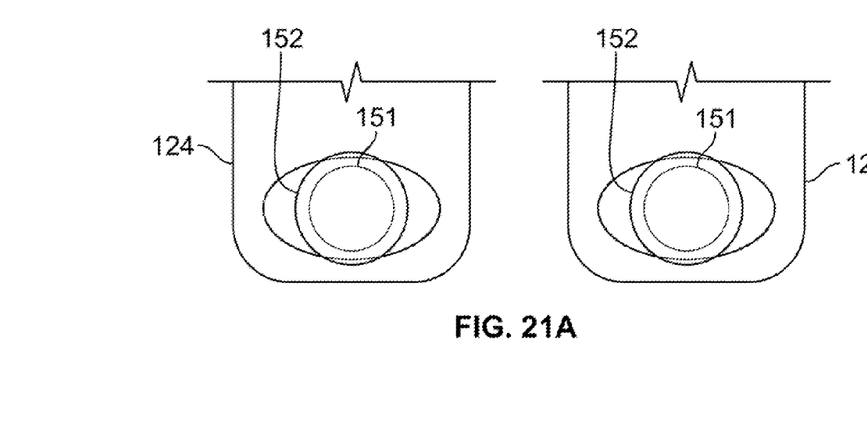
FIG. 21A shows the advance of the pins so that the large diameter portions of the pins are in the pin holes to become locked therein.
Figure 21B:
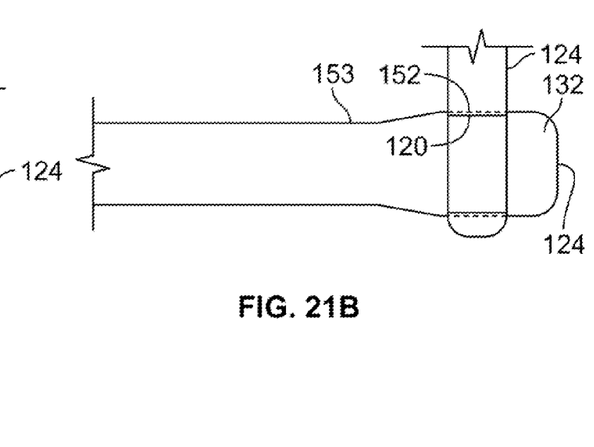
FIG. 21B is a side view of FIG. 21A showing the pin in the pin hole.

FIG. 21A shows the entry of the larger diameter portion 152 into the hole 120 to its fully inserted position as shown in FIG. 21B in which the cross-piece 132 is seated on the legs 124 of the pin plate 114.

Figure 22A:
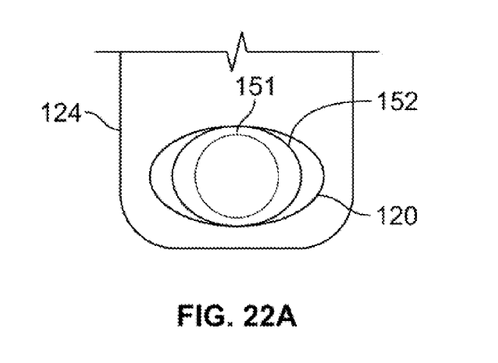
FIG. 22A is an explanatory view that shows the deformation of the pin when locked in the hole as shown in FIGS. 21A, B.
Figure 22B:
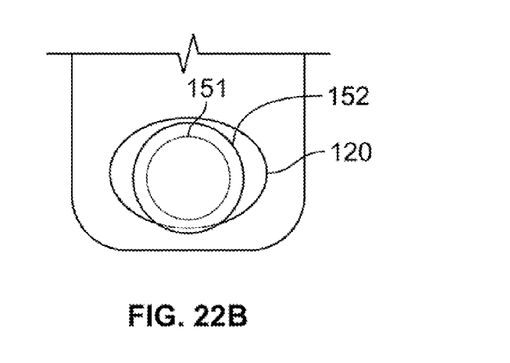
FIG. 22B is similar to FIG. 21A except showing the distortion of the hole in the locked position of the pin.

The second portion 152 has a diameter at least equal to and preferably slightly greater than the length of the minor axis B of the pin and becomes lockably fixed in the hole with an interference fit. In part this is due to the different shapes of the circular pin and the elliptical hole and due to one or both of two different mechanisms. On the one hand, as shown in FIG. 22B, the large portion of the pin deforms the hole causing increased length along the minor axis B and shortening of the hole along the major axis A while, on the other hand, as shown in FIG. 22A the pin itself undergoes elastic deformation to fit in the hole by shortening along its Y axis and lengthen it along its X axis to assume an elliptical shape.

By way of example, the holes 120 are machined with close tolerances to have a smaller dimension along its minor axis of 0.067" and a larger dimension along its major axis of 0.087". The pin is machined with close tolerances with the first portion having a diameter of 0.061" and the second portion having a diameter of 0.068".

Although the first and second portions of the pin have been shown as circular in cross section other shapes are possible. All that is required for the first section 151 is that it be smaller than the hole in all directions and the second section 152 be close in size to the dimension of the pin hole along the minor axis. The cross sectional shape of the first and second portions of the pin is not limiting and other cross sectional shapes are possible, such as oblong, elliptical, truncated and the like.

Figure 23:
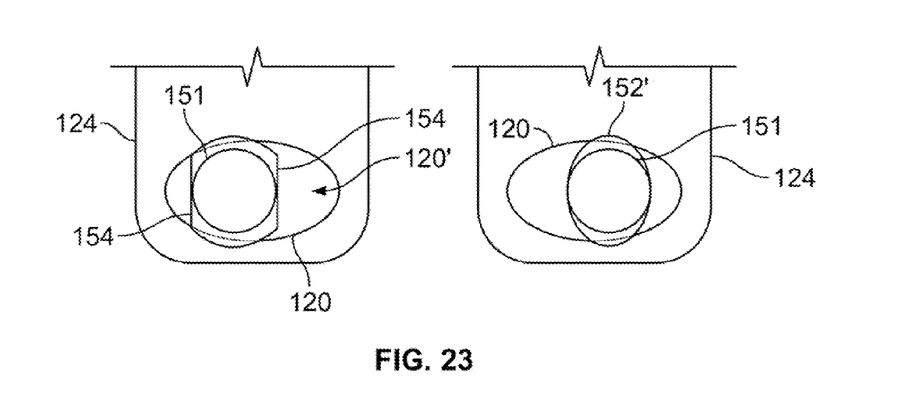
FIG. 23 diagrammatically shows in cross-section variations in the cross sectional shape of the pins.

FIG. 23 shows a diagrammatic cross section of a pin 120' in which the first portion 151 is circular and the second portion 152 is part-circular with flat truncated sides 154.

In order to expedite insertion of the U-pin into the pin holes, the cross piece 32 can be located outside the plane of the pins in all of the disclosed embodiments.

Although the invention has been described in relation to specific embodiments thereof it would become apparent to those skilled in the art that numerous modifications and variations can be made within the scope and spirit of the invention.

The invention claimed is:

1. A pin plate assembly comprising:
a pin plate adapted for being secured to a bone, said pin plate having at least a first pin hole extending therethrough,
a pin member comprising a pin,
said pin being insertable in said at least first pin hole to extend therethrough to an operative position in which a first portion of the pin engages a fragment of the bone,
said pin comprising a plurality of portions, including the first portion and a second portion, arranged to enter said pin hole in succession as the pin is longitudinally advanced in the pin hole from a first position, wherein the first portion has not yet advanced through the pin plate, to the operative position, wherein the first portion has advanced through the pin plate and engaged the bone fragment, said first portion having a shape and dimension with respect to said pin hole, including a diameter that is smaller than a diameter of the pin hole, so as to travel substantially freely through the pin hole from the first position to the operative position as the pin is longitudinally advanced in the pin hole, said second portion being shaped and dimensioned with respect to said pin hole such that the second portion enters but does not exit the pin hole when the pin is longitudinally advanced into the pin hole from the first position to the operative position, respective dimensions of said pin and pin plate being such that the pin, the pin plate or both elastically deform when the second portion is longitudinally advanced into the pin hole so that the second portion of the pin engages the pin plate in an interference fit when the second portion is positioned in the pin hole.

2. The pin plate assembly as claimed in claim 1, wherein said pin hole has an elongated cross section with a major and a minor axis, the cross section of the first portion of the pin has a maximum dimension aligned with the minor axis of the pin hole which is not greater than the dimension of the pin hole along the minor axis thereof.

3. The pin plate assembly as claimed in claim 2, wherein said second portion of the pin has a minimum cross section aligned with the minor axis of the hole which is not less than the dimension along the minor axis of the hole.

4. The pin plate assembly as claimed in claim 3 wherein the cross sections of the first and second portions of the pin are circular.

5. The pin plate assembly as claimed in claim 3, wherein said elongated cross section of the pin hole is substantially elliptical.

6. The pin plate assembly as claimed in claim 3, wherein said pin includes a transition portion joining said first and second portions, said transition portion having a lower end with a diameter that is substantially equal to the diameter of the first portion and an upper end with a diameter that is substantially equal to the diameter of the second portion.

7. The pin plate assembly as claimed in claim 1, wherein said second portion of the pin has resilience.

8. The pin plate assembly as claimed in claim 7 wherein said second portion of the pin includes a cross piece that connects said pin with a second pin of the pin member.

9. The pin plate assembly as claimed in claim 8, wherein the pin and the second pin are spaced apart a distance and the plate comprises a second pin hole in addition to said first pin hole, wherein the first and second pin holes are spaced apart and are elongated laterally to enable the pin and second pin to freely pass through the respective first and second pin holes in the pin plate.

10. The pin plate assembly as claimed in claim 9, wherein the holes in the plate are elliptical and the first portion of the pins are circular in cross-section.

11. The pin plate assembly as claimed in claim 8, wherein said second pin is insertable into a respective said pin hole provided in the pin plate and includes respective said first and second portions and a locking mechanism to secure the second pin in the respective pin hole and oppose relative movement of the second pin in relation to its respective pin hole.

12. The pin plate assembly as claimed in claim 11, wherein said pin and said second pin are capable of resilient displacement, and the pin and second pin are disposed with respect to the pin holes and to each other such that the pin and second pin are resiliently displaced when the pin and second pin are inserted into the pin holes.

13. The pin plate assembly as claimed in claim 12, wherein the cross-piece has a diameter different from the diameter of each of the pins.

14. The pin plate assembly as claimed in claim 1, wherein the first portion of the pin is slidable in the pin hole and is substantially restrained by the plate from translation in the plane of the plate and from angular movement in the pin hole when the second portion of the pin is inserted in the pin hole.

15. The pin plate assembly as claimed in claim 1, wherein said pin member includes two said pins and a cross piece joining said pins, to form the pin member with a U shape.

16. The pin plate assembly as claimed in claim 15, wherein said pin plate has an end with a U shaped opening therein defining spaced legs on opposite sides of the U-shaped opening, said pin holes being in said legs.

17. The pin plate assembly as claimed in claim 16, wherein said cross piece of the pin member of U shape has a dimple therein to fit in said opening between said legs of the pin plate when the pin of U shape is seated on the pin plate in said operative position.

18. The pin plate assembly as claimed in claim 1, wherein said pin hole in said plate has an axis disposed at an angle relative to a plane of the plate.

19. The pin plate assembly as claimed in claim 1, wherein said pin plate elastically deforms to lock said pin when the second portion is seated in said pinhole.

20. The pin plate assembly as claimed in claim 1, wherein said pin elastically deforms to lock said pin when the second portion is seated in said pin hole.

21. In a pin plate assembly in which a pin member is engaged in pin holes in the pin plate to engage and secure a fractured bone fragment and become locked in the pin plate, the improvement wherein the pin member is formed as a U shaped member comprising two spaced legs and a cross-piece connecting the legs to confer the U shape to the pin member, each of the two spaced legs comprising a first distal portion and a second proximal portion, the first distal portion of at least one of the legs being dimensioned and shaped to constitute means for freely passing through a respective said hole when said at least one leg is longitudinally advanced through the hole to engage the bone fragment and the second proximal portion of the at least one leg being dimensioned and shaped to constitute means for preventing the second proximal portion of the at least one leg from exiting through the pin hole when the first distal portion and the second proximal portion of the at least one leg are longitudinally advanced in sequence into said respective hole from a first position, wherein the first distal portion of the at least one leg has not yet advanced through the pin plate to an operative position, wherein the first distal portion of the at least one leg has advanced through the pin plate and engaged the bone fragment, said pin member and pin plate being constructed and arranged such that the second proximal portion of the at least one leg, the pin plate or both elastically deform when the second proximal portion of the at least one leg is longitudinally advanced into the respective pin hole such that the second proximal portion of the at least one leg engages the pin plate with an interference fit to lock the pin member in the pin plate and to oppose relative movement between the pin member and the pin plate and withdrawal of the pin member from the pin plate.

22. The improvement as claimed in claim 21, wherein said first distal portion of the at least one leg is dimensioned and shaped to fit in the respective hole to have lateral clearance therein for permitting U shaped pins with legs of different spacing to pass freely through the respective hole.

23. The improvement as claimed in claim 21, wherein said at least one leg includes a transition portion between said first distal portion and said second proximal portion, said transition portion having a first end joined to the first distal portion, the first end having substantially the same cross-sectional shape and dimension as the first distal portion, said transition portion having a second end joined to the second distal portion, said second end having substantially the same cross-sectional shape and dimension as the second distal portion.

24. The improvement as claimed in claim 21, wherein said pin plate has an end with a U shaped opening therein defining spaced legs on opposite sides of the U-shaped opening, said pin holes being in said legs, and wherein said cross piece of the pin member of U shape has a dimple therein to fit in said opening between said legs of the pin plate when the pin of U shape is seated on the pin plate in an operative position.

* * * * *